(12) United States Patent
Wager (10) Patent No.: US 11,404,161 B2
(45) Date of Patent: Aug. 2, 2022

(54) SYSTEM AND METHOD FOR CLINICAL WORKFORCE MANAGEMENT INTERFACE

(71) Applicant: CERNER INNOVATION, INC., Kansas City, KS (US)

(72) Inventor: Douglas W. Wager, Kansas City, MO (US)

(73) Assignee: CERNER INNOVATION, INC., North Kansas City, MO (US)

(*) Notice: Subject to any disclaimer, the term of this patent is extended or adjusted under 35 U.S.C. 154(b) by 1185 days.

(21) Appl. No.: 15/394,209

(22) Filed: Dec. 29, 2016

(65) Prior Publication Data

US 2017/0140112 A1 May 18, 2017

Related U.S. Application Data

(62) Division of application No. 11/025,969, filed on Jan. 3, 2005, now abandoned.

(51) Int. Cl.
*G16H 40/20* (2018.01)
*G06Q 10/10* (2012.01)
(Continued)

(52) U.S. Cl.
CPC ............ *G16H 40/20* (2018.01); *G06Q 10/10* (2013.01); *G06Q 10/109* (2013.01); *G16H 40/63* (2018.01); *G16Z 99/00* (2019.02)

(58) Field of Classification Search
None
See application file for complete search history.

(56) References Cited

U.S. PATENT DOCUMENTS 4,769,796 A 9/1988 Levine
5,809,477 A 9/1998 Pollack
(Continued)

FOREIGN PATENT DOCUMENTS

CA 2226612 A1 * 4/1999 ....... G06Q 10/06314

OTHER PUBLICATIONS

Dugdale, D C et al. "Time and the patient-physician relationship." Journal of general internal medicine vol. 14 Suppl 1, Suppl 1 (1999): S34-40. doi:10.1046/j.1525-1497.1999.00263.x (Year: 1999).*

*Primary Examiner* — Lena Najarian
(74) *Attorney, Agent, or Firm* — Shook, Hardy & Bacon, L.L.P.

(57) ABSTRACT

Systems and methods for generating and presenting a clinical workforce management interface to assign staff in a clinical setting. The interface may present components including an aggregate patient population profile listing individual patients in a unit, the projected workload capacity the care for those patients represents, and an assignment bar depicting provider assignments for that patient over a designated time period. The interface may likewise present a provider population profile which lists available care providers in a unit, as well as their capacity ratings, skill sets, shifts, or other schedule data characterizing available clinical staff. A charge nurse or other staff manager may view and manipulate the provider-to-patient assignments, for instance by dragging and dropping visual elements to perform assignments. Compliance monitoring functions such as maintaining provider ratios may be automatically performed, and the staff manager may be alerted when ratios or criteria violate limits.

8 Claims, 4 Drawing Sheets

(51) Int. Cl.
*G16H 40/63* (2018.01)
*G16Z 99/00* (2019.01)

(56) References Cited

U.S. PATENT DOCUMENTS

| | | |
|---|---|---|
| 5,842,173 A | 11/1998 | Strum et al. |
| 5,995,937 A | 11/1999 | Debusk et al. |
| 6,014,629 A | 1/2000 | Debruin |
| 6,061,657 A | 5/2000 | Whiting et al. |
| 6,193,654 B1 | 2/2001 | Richardson et al. |
| 6,302,844 B1 | 10/2001 | Walker et al. |
| 6,314,556 B1 | 11/2001 | DeBusk et al. |
| 7,076,436 B1 | 7/2006 | Ross, Jr. et al. |
| 7,155,399 B2 | 12/2006 | Andre et al. |
| 2002/0032584 A1 | 3/2002 | Doctor et al. |
| 2002/0046062 A1 | 4/2002 | Kameda |
| 2002/0072911 A1 | 6/2002 | Kilgore et al. |
| 2002/0133386 A1* | 9/2002 | Chishti ............... G06Q 10/10 705/7.29 |
| 2003/0050797 A1 | 3/2003 | Brandt et al. |
| 2003/0050801 A1 | 3/2003 | Ries et al. |
| 2003/0066032 A1* | 4/2003 | Ramachandran ... G06F 3/04847 715/234 |
| 2003/0074222 A1 | 4/2003 | Rosow et al. |
| 2003/0101076 A1 | 5/2003 | Zaleski |
| 2003/0220815 A1 | 11/2003 | Chang et al. |
| 2004/0039628 A1* | 2/2004 | Thompson ......... G06Q 10/0631 705/2 |
| 2004/0267585 A1 | 12/2004 | Anderson et al. |
| 2005/0075902 A1 | 4/2005 | Wager et al. |
| 2005/0075904 A1 | 4/2005 | Wager et al. |
| 2005/0182657 A1 | 8/2005 | Abraham-Fuchs et al. |
| 2005/0234741 A1 | 10/2005 | Rana et al. |
| 2006/0047553 A1 | 3/2006 | Fuhrmann et al. |
| 2006/0047554 A1 | 3/2006 | Larsen et al. |
| 2006/0053044 A1 | 3/2006 | Kurian et al. |
| 2006/0074740 A1 | 4/2006 | Garcia et al. |
| 2006/0143060 A1 | 6/2006 | Conry et al. |
| 2006/0143061 A1 | 6/2006 | Sharper et al. |
| 2007/0226010 A1 | 9/2007 | Larsen |

\* cited by examiner

Warning!
This assignment will cause Leslie Bryant to have 5 patients for the hours of 12:00-1:00. The maximum patients per care provider allowed in this unit is 4. You may:

Continue, and fix later    Cancel Assign

SYSTEM AND METHOD FOR CLINICAL WORKFORCE MANAGEMENT INTERFACE

CROSS-REFERENCE TO RELATED APPLICATION

This application is a divisional of co-pending U.S. patent application Ser. No. 11/025,969, filed on Jan. 3, 2005, entitled "System and Method for Clinical Workforce Management Interface," which is related to the subject matter of U.S. patent application Ser. No. 10/679,836 filed Oct. 6, 2003, entitled "Computerized System and Method for Determining Work in a Healthcare Environment"; and to the subject matter of U.S. patent application Ser. No. 10/917,337 filed Aug. 13, 2004, entitled "System And Method For Automatically Generating Evidence-Based Assignment Of Care Providers To Patients", each of which applications is assigned or under obligation of assignment to the same entity as this application, and each of which applications is incorporated by reference herein.

STATEMENT REGARDING FEDERALLY SPONSORED RESEARCH OR DEVELOPMENT

Not applicable.

FIELD OF THE INVENTION

The invention relates to the field of clinical information technology, and more particularly to a system and method for a management interface which presents a charge nurse or other staffing manager with an intuitive, visual interface for generating patient-to-care provider assignments, including capacity computation, skill set matching, ratio management and other parameters as part of that interface.

BACKGROUND OF THE INVENTION

The healthcare environment continues to demand increased attention to and emphasis on clinical workforce management, including to deploy nurses, technicians, rehabilitation and other staff with better efficiency and clinical efficacy. Hospitals and other clinical sites furthermore may find themselves operating under federal, state or other compliance requirements which demand that the ratio of care providers to assigned patients adhere to specified ratios or that the staffing level is appropriate for the level of acuity of the relevant patient population. Those regulatory considerations combined with operational needs such as the need to continuously mix and adjust provider assignments under day to day schedule changes such as vacation time, lunch and other breaks, sick days, and other absences or developments make the task of promulgating shift-by-shift patient assignments a challenging one, for charge nurses and other clinical managers tasked with staffing duties.

Those staff managers moreover are frequently confronted with the need to generate provider/patient assignments with no formal or computerized tools to assist in that workforce management. Charge nurses or other unit or other managers thus must frequently rely on manual notes, memory and intuition to assemble a staff schedule and make appropriate provider-to-patient assignments on an ad hoc or short-term basis. Staff managers may moreover often have little time to generate such a floor schedule for the next shift, week or other period even on a manual basis. Other problems in clinical workforce management exist.

SUMMARY OF THE INVENTION

The invention overcoming these and other problems in the art relates in one regard to a system and method for a clinical workforce management interface, in which a staff manager may be presented with a suite of provider assignment options and alternatives, to automatically organize and drive assignment ratios and other assignment parameters and options with compliance, capacity, best practice and other criteria taken into account. According to embodiments of the invention in one regard, a visual or graphical interface or other presentation layer may present a charge nurse or other staff manager with a patient list including graphical or iconic representations of the continuity and types of assigned provider care for each patient, for instance in a slider bar showing continuity of provider assignments or any gaps therein, for example over a shift, 24 hours, week or other periods. In embodiments, the assignment bar, provider names, icons or other visual elements or objects may be manipulated, for instance dragged and dropped, to effect assignments, changes to assignments or other actions. The interface may likewise indicate the acuity or amount of work which a given patient's care will demand of a provider, and generate aggregate totals of the amount of capacity in a clinical unit available to serve the patient population. Mandated patient-to-provider ratios may automatically be monitored, and alerts may be presented when those or other compliance, operational or other criteria are violated. Because in one regard an entire range of workforce management functions may be integrated in one interface, and that interface or tool may automatically present and analyze core capacity and other variables and options, as well as store resulting assignments and schedules to distribute to staff and form a basis for or input to further schedules, the overall task of timely workforce assignments may be achieved more efficiently, compliance may be better ensured while capacity may be more effectively managed against fluctuating clinical demands.

DETAILED DESCRIPTION OF EMBODIMENTS

Figure 1:
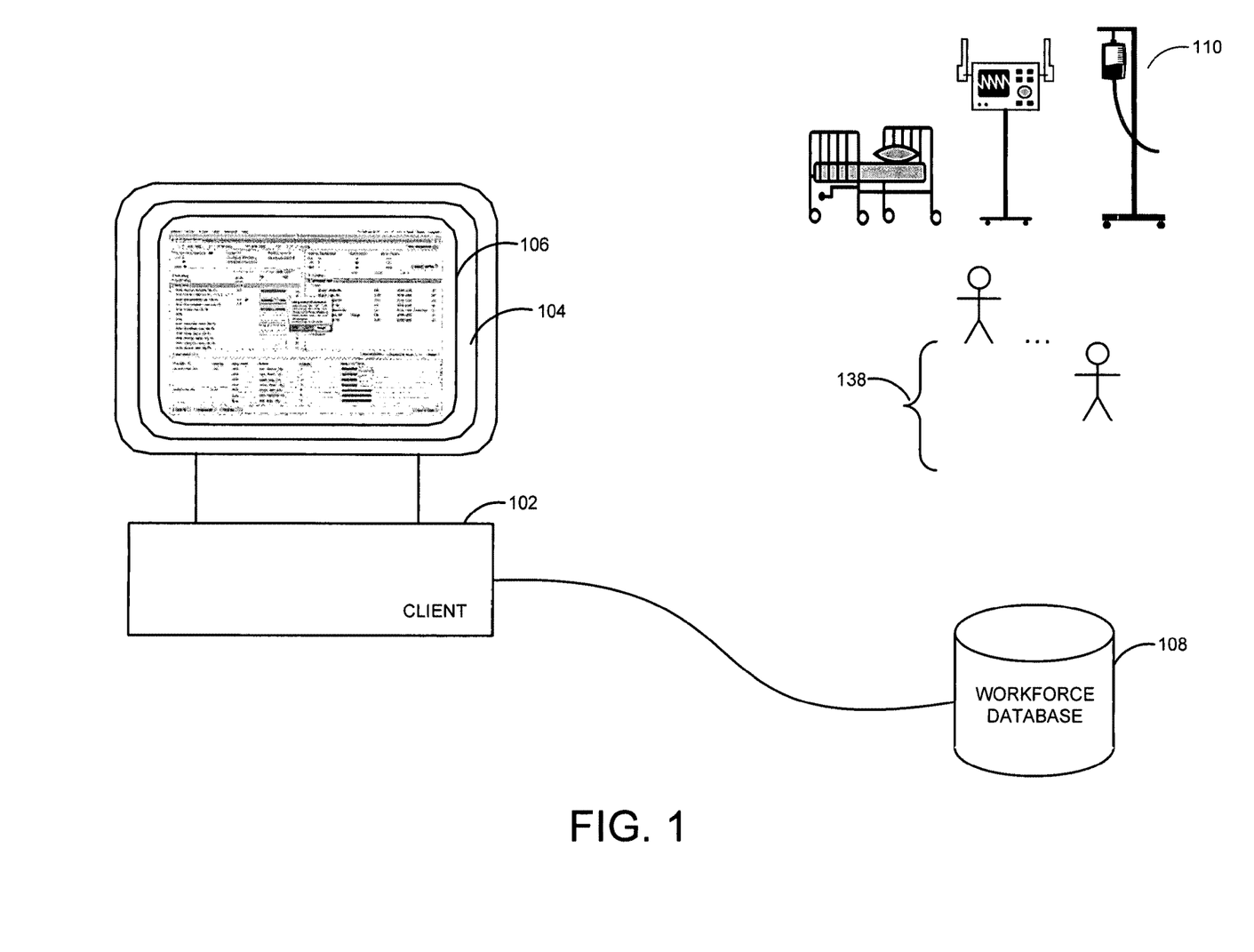
FIG. 1 illustrates a clinical workforce environment in which a system and method for a workforce management interface may operate, according to embodiments of the invention.

FIG. 1 illustrates an environment in which a system and method for a clinical workforce management interface may operate, according to embodiments of the invention. As illustrated in that figure, a charge nurse or other personnel or staff manager may operate a client 102 having a graphical user interface 104 to initiate, access or execute a workforce management interface 106. The staff manager may access the workforce management interface 106 before, during or after a work shift for a unit 110 such as an emergency room, acute care unit, post-operative unit or other section, division, department, floor or other organizational unit of a hospital or other clinical care facility. The staff manager may operate the workforce management interface 106 to schedule shifts, generate care provider-to-patient assignments, review capacity loads and perform other personnel or staffing duties with respect to a care provider staff 138 which may be or include, for example, nurses, therapists, technicians, physicians, interns, or other clinical or other personnel whose responsibilities or activities are directed to or associated with patients in unit 110, or otherwise.

Figure 2:
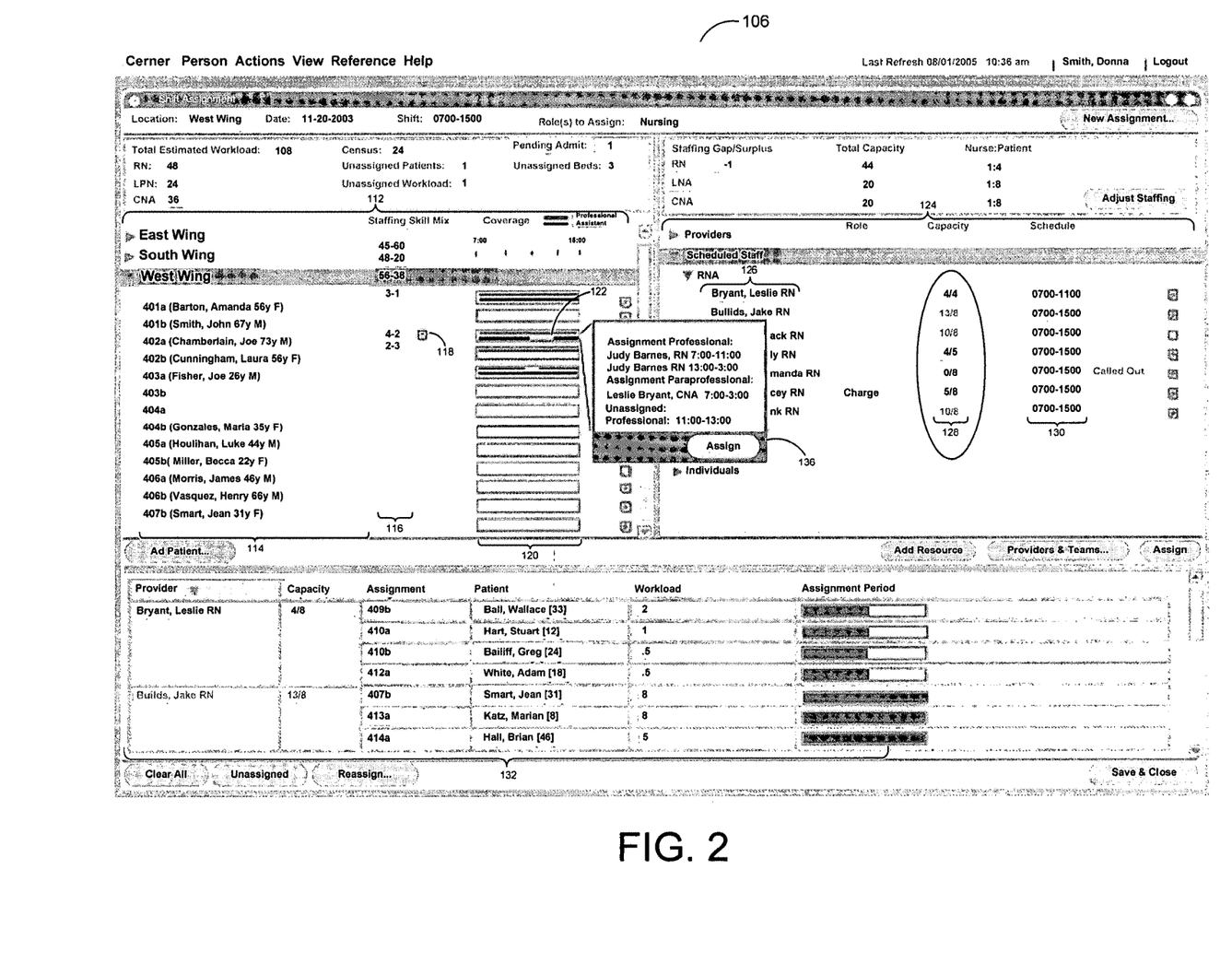
FIG. 2 illustrates a workforce management interface, according to embodiments of the invention.

According to embodiments of the invention as for example illustrated in FIG. 2, the workforce management interface 106 may include a range of views including graphical and numerical or textual indicators, activatable icons and other objects and resources to organize and visually present provider assignment information, in an integrated presentation layer or interface. According to embodiments as shown, those resources may include a patient population profile 112 which may be or include, for instance, a patient list 114 or other census or other enumeration of patients within unit 110, or other grouping. The patient population profile 112 may include, for further example, a patient needs rating 116 indicating the rated amount of workload or work effort represented by a patient's care, for instance expressed in normalized units of person-hours, or other quantities or units. The patient population profile 112 may further include a set of skill criteria 118, for instance indicating that the care of a particular patient requires specialized training, certification or skills, for example the training or competence to operate a high-frequency ventilator, or other skills.

According to embodiments of the invention in a further regard, and as likewise illustrated in FIG. 2, the patient population profile 112 may likewise include an assignment bar 120, which may in one regard depict or represent the presence, absence or type of care provider assignment or coverage for a given patient in patient list 114, over a scheduled period of time. For instance, the assignment bar 120 may indicate that for an eight-hour shift from 11 p.m. to 7 a.m. or other period, the patient is covered by assignment of a primary care nurse, or other personnel. Conversely, if a patient does not have a designated care provider for that or other period, the assignment bar 120 may display a gap 122, such as a white or other visually distinct color or segment, to indicate that a patient has not received an assignment of a care provider for the represented period. According to embodiments of the invention in a further regard, the assignment bar 120 may be activatable, for example by highlighting or clicking, to display an expanded assignment view 136 which presents details on a particular patient's provider assignment or assignments and related information, including for instance the category of provider (e.g. professional), time period ranges for that provider, and the name or other identifier for that provider. Other data may be presented in expanded assignment view 136.

According to embodiments of the invention as illustrated in FIG. 2 in another regard, the workforce management interface 106 may likewise include views and resources directed to the pool of available care providers, including a provider population profile 124 which may contain a provider list 126 which may identify available care providers by name, or other designation. Provider population profile 124 may further contain a set of provider capacity ratings 128 which may indicate a given nurse's, therapist's, technician's or other person's capacity to undertake patient care, for instance expressed in person-hours of care, or other units. According to further embodiments of the invention, the provider capacity ratings 128 may include or incorporate a scaling or adjustment factor to take a given provider's experience level, specialized training, patient continuity and other factors into account, in rating the amount of normalized patient care that provider may contribute. According to embodiments of the invention in one regard, the provider capacity ratings 128 or other projected or estimated work capacity or production ratings may be generated by or accessed from a capacity platform or engine such as that described in the aforementioned U.S. patent application Ser. No. 10/679,836, or other platforms, systems or resources. Other computations or expressions of capacity in provider capacity ratings 128 are possible.

Provider population profile 124 as illustrated in FIG. 2 may further include a provider schedule 130 for care providers in provider list 126, for instance indicating a provider's availability or expected presence for a given shift for certain hours of the day, or for other times or periods. According to embodiments of the invention in one regard, the workforce management interface 106 may permit a charge nurse or other staff manager to manipulate data, icons and other objects to assign, update, reassign, review and otherwise process a set of provider-to-patient (or patient-to-provider) assignments, in one regard in a visually comprehensible fashion. For example, a staff manager may determine that a patient inpatient list 114 lacks an assigned provider for a shift from 7 a.m. to 3 p.m. for a given day. The manager or other operator may then highlight, grab, click or otherwise activate a provider name in provider list 126, and drag and drop that identifier onto assignment bar 120 for that patient, or otherwise associate the provider with the patient. In another embodiments, the user may select one or more patients and one or more providers, and initiate an automated assignment process such as the system and method described in the aforementioned U.S. patent application Ser. No. 10/917,337, or others. According to embodiments of the invention in one regard, the assignment bar 120 may automatically change appearance, for instance to be grayed in, to indicate care coverage from 7 a.m. to 3 p.m. Other visual, graphical or other indications or encodings are possible. According to embodiments of the invention in one regard, that assignment may be automatically generated, graphically presented and data such as provider capacity ratings 128 may be automatically updated, upon the registration of a new assignment in that drag and drop or other fashion. Other icons, objects and actions are possible.

According to embodiments of the invention illustrated in FIG. 2 in another regard, the workforce management interface 106 may likewise present a staff capacity breakdown 132 to present to the staff manager the total allocation of staff capacity during a given shift or other period in summary fashion, for instance to list providers in a table with their assigned patients and workload allocations. Other views, tabulations or reports are possible.

Figure 3:
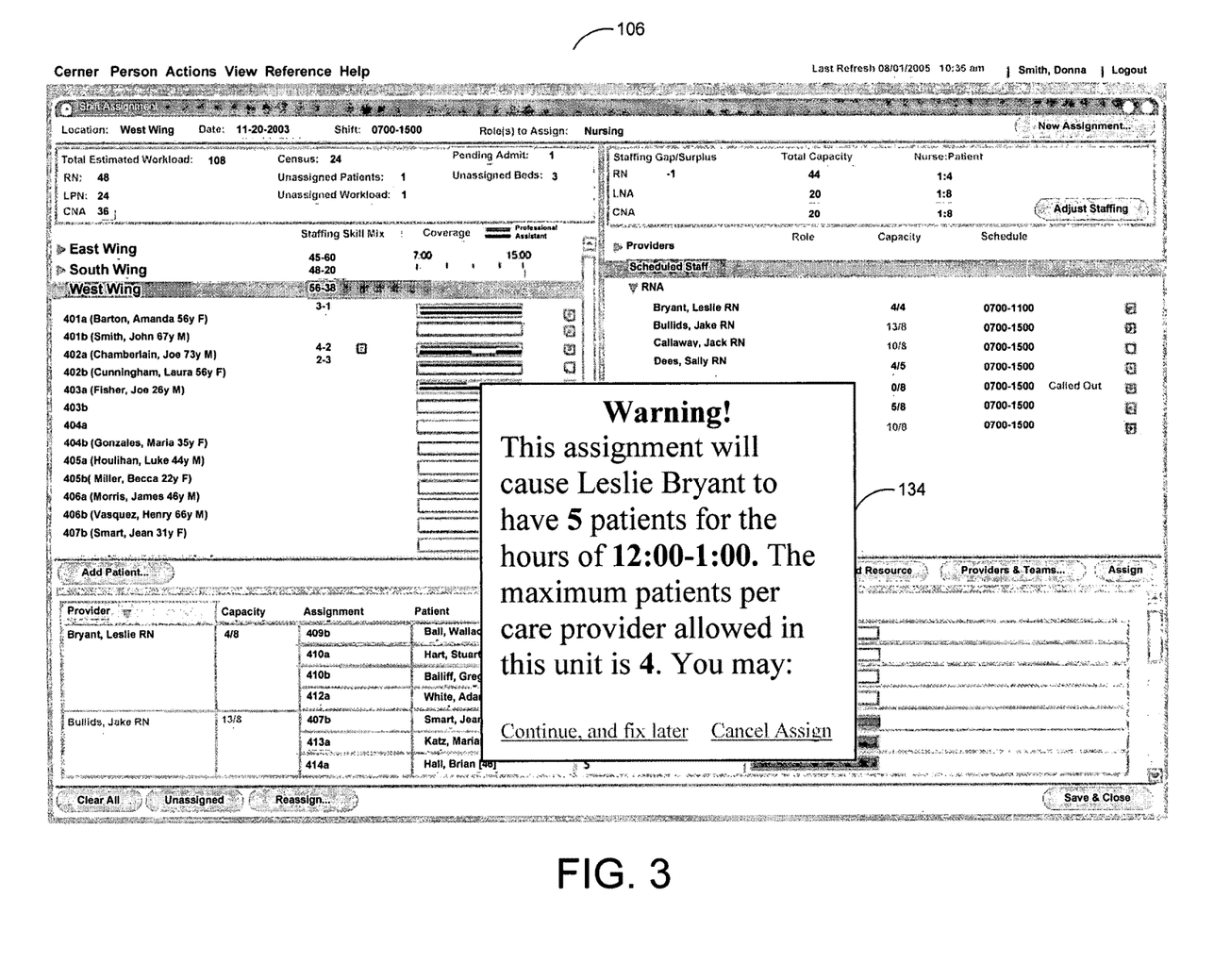
FIG. 3 illustrates a workforce management interface including an alert, according to embodiments of the invention.

According to embodiments of the invention in a further regard, the workforce management interface 106 and associated logic may further monitor or condition patient assignments based on regulatory compliance, clinical best practices or other clinical or operational criteria. Thus for example, and as for example illustrated in FIG. 3, the workforce management interface 106 may monitor for mandatory or other state, federal, industry or other compliance criteria regarding or limiting the acceptable ratio of care providers to patients or requiring staffing based on quantitative levels of acuity. When an attempt is made, for instance by selecting, dragging and dropping a care provider by name to an assignment bar 120 for a patient which would result in that provider's reaching a level of, for example, five (or other) patients for a given shift or period, the workforce management interface 106 may generate and display an alert 134 indicating that exception to a charge nurse or other manager. According to embodiments, in the event of an alert 134 the workforce management interface 106 may present the staff manager (or other user) with options for instance to temporarily accept an assignment to remedy the violation later, to cancel that assignment, to suggest alternative assignments, or take other actions or options. Other regulatory, compliance, clinical, operational, industry or other criteria or guidelines may be used, monitored or accessed to trigger alert 134.

Figure 4:
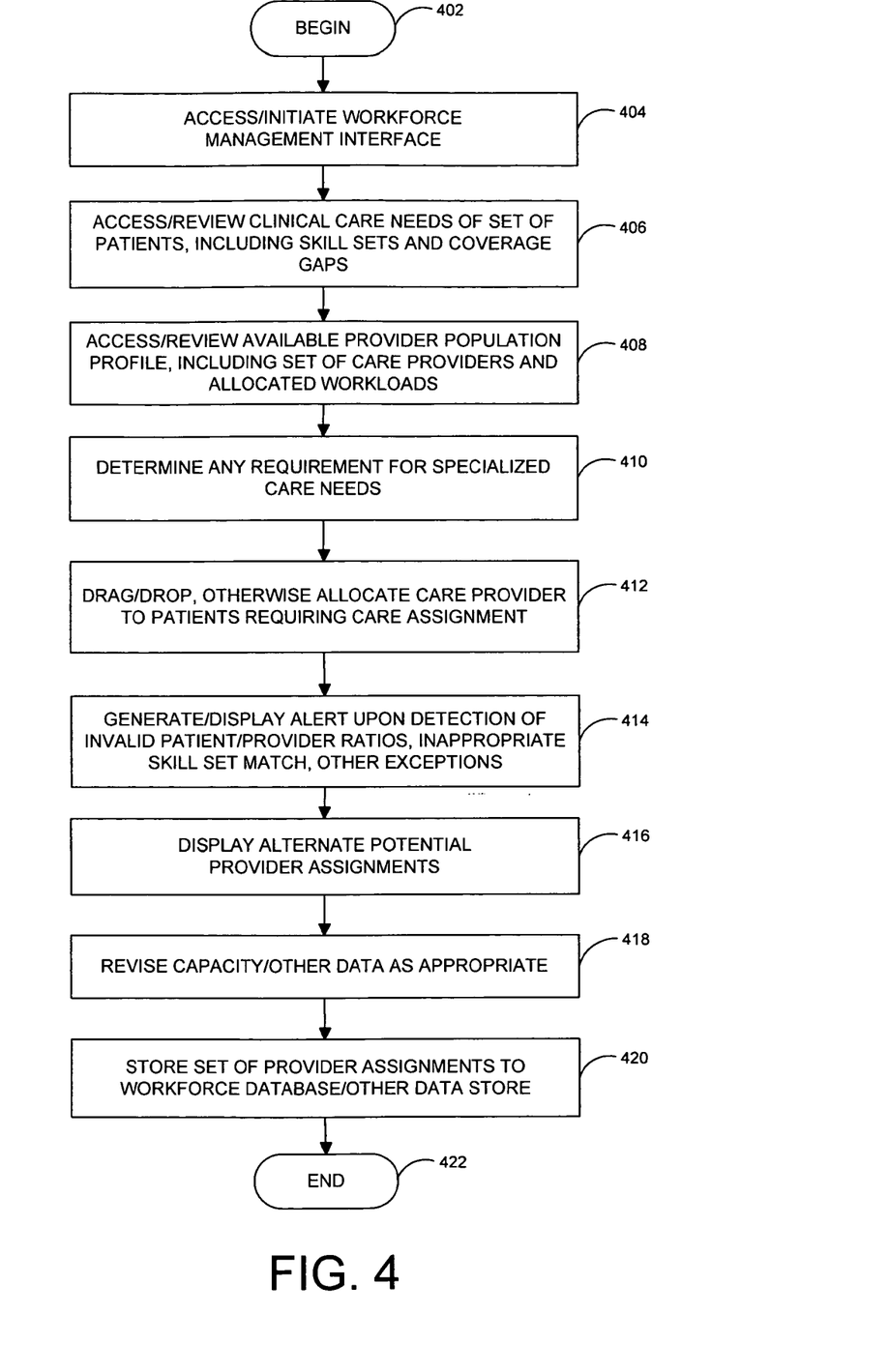
FIG. 4 illustrates a flowchart of overall workforce management and interface processing, according to embodiments of the invention.

FIG. 4 illustrates overall management interface and workforce assignment processing, according to embodiments of the invention. In step 402, processing may begin. In step 404, the workforce management interface 106 or other clinical tool, interface, presentation layer or resource may be accessed, initiated or executed, for example by a charge nurse on or by client 102 or other networked or other machine or resource. In step 406, the charge nurse or other staff manager may access or review the patient population profile 112 to assess or determine the clinical care needs of patients in a unit or other group represented in patient population profile 112. Those clinical care needs may be or include specialized skill criteria 118 required to service the conditions or carry out the therapies of individual patients, such as for example training on or certification for types of equipment such as ventilators or pumps, electrocardiograms (EKGs), the training or certification to insert and administer intravenous lines, or other qualifications, skills, certifications or capabilities.

Those clinical care needs may likewise include provider coverage or assignment gaps, for instance depicted in assignment bar 120 as a white-colored or other coverage gap 122 indicating, for instance, that an assigned nurse, therapist or other care provider is scheduled to depart early on a given day, leaving four hours starting at noon or other periods of time for that patient uncovered or unassigned. Other care assignments and patient needs are possible.

In step 408, the staff manager may review the provider population profile 124 to assess and determine available care providers and their projected or estimated capacities, skill sets and other information or qualifications to service the patient population. For instance, a charge nurse or other staff manager may use workforce management interface 106 to access the provider population profile 124 and review provider list 126, provider capacity ratings 128, provider schedule 130 and other information to assess the overall complement of provider capacity and capability available for assignment. According to embodiments of the invention in one regard, the provider capacity ratings 128 or other projected or estimated work capacity or production ratings may be generated by or accessed from a capacity platform such as that described in the aforementioned U.S. patent application Ser. No. 10/679,836, or other platforms, systems or resources.

In step 410, the staff manager may assess and determine any requirement for specialized care needs, such as for example the assignment of common care providers to a mother and newborn infant. In step 412, the staff manager may drag and drop or otherwise allocate or activate an assignment of a care provider to one or more patient requiring a care assignment, for instance selecting or highlighting a nurse, therapist, technician or other from provider list 126 and dragging that name or other object on top of a patient name in the patient list 114. According to embodiments of the invention in one regard, upon acceptance of that selected assignment, the assignment bar 120 and other graphical displays or other information may be updated to reflect the newly assigned provider, and the period of time over which they may be assigned. According to embodiments of the invention in a further regard, the coverage gap 122 may automatically disappear when such an assignment may be made. In other embodiments of the invention, when a patient is selected in step 412, the system may block off all or part of one or more assignment bars for the staff who are inappropriate based on the patient's rated needs and the provider's rated capacity.

In step 414, an alert 134 may be generated and displayed on workforce management interface 104 upon the detection or identification of an assignment, attempted assignment or other action causing or leading to violation of compliance, clinical, operational or other criteria or limits, for instance upon detection of a skill set mismatch or other exception, or that the assignment of a nurse would result in a patient assignment total or ratio which would exceed federal, state, industry or other limits or guidelines. In step 416, the workforce management interface 106 may in the event of an invalid assignment or other exception generate an alternative provider assignment which may remove the exception or other invalid condition.

In step 418, the workforce management interface 106 may generate and display updated assignment, capacity, schedule and other data reflecting provider assignment updates or changes and other information, for instance via assignment bar 120 or other visual, graphical or other display. In step 420, the set of provider assignments 132 may be stored to workforce database 108 or other data store or facility, for instance to distribute to the clinical staff, create a record of clinical operations, to serve as a basis for or input to a further set of assignments, or other purposes. In step 422, processing may repeat, return to a prior processing point, jump to a further processing point or end.

The foregoing description of the invention is illustrative, and modifications in configuration and implementation will occur to persons skilled in the art. For instance, while the invention has generally been described in terms of generating and presenting a workforce management interface 106 which may be hosted on or displayed by a client 102 such as a desktop or laptop computer, in embodiments the workforce management interface 106 may be hosted on, executed by or displayed on other machines or resources, for instance on a network-enabled cellular telephone or digital assistant, a special-purpose workstation, or other hardware or resources.

Similarly, while the invention has in embodiments been described as involving the tracking and management of patient assignment configurations in a single unit 110 such as a single hospital floor or department, in embodiments the workforce management interface 106 may track, manage and provide a view on other units of operation or multiple units, such as a wing, laboratory, complete floor, or other workforce or workplace section or division, combinations of the same, or multiple or aggregated hospitals or other facilities. Other hardware, software or other resources described as singular may in embodiments be distributed, and similarly in embodiments resources described as distributed may be combined. For instance while the invention has in embodiments been described as storing patient assignment and other data to a single workforce database 108, in embodiments patient data, provider data, patient to provider (or provider to patient) assignment and other data may be stored to single or multiple local, remote, networked or other databases or data stores. The scope of the invention is accordingly intended to be limited only by the following claims.

I claim:

1. A system for managing clinical workforce operations comprising:
   at least one computing device, having a processor coupled to a memory, communicating with a database and one or more client devices operated respectively by one or more operators, wherein the at least one computing device accesses the database and communicates with the one or more client devices, wherein the one or more client devices operate in a network with the at least one computing device, and each of the one or more client devices has a processor coupled to a memory;
   the at least one computing device provides instructions to the one or more client devices, wherein the one or more client devices generate a graphical user interface;
   wherein the at least one computing device receives one or more indications of the one or more operators' interactions respectively with the graphical user interface at the one or more client devices and do the following:
      access at least one clinical care need of a patient, wherein the at least one clinical care need includes a skill set required to service a need of the patient;
      access a healthcare provider population profile from the database through the at least one computing device, wherein the healthcare provider population profile includes availability of at least one healthcare provider, a skill set of the at least one healthcare provider, and a healthcare provider capacity rating of the at least one healthcare provider;
      receive a selection of the at least one healthcare provider such that the at least one healthcare provider is assigned to the patient and the assignment is displayed at the graphical user interface based on a period of time that the at least one healthcare provider is assigned to the patient; wherein the selection of the at least one healthcare provider includes dragging and dropping a healthcare provider identifier object associated with the at least one healthcare provider on a patient identifier object associated with the patient at the graphical user interface at the one or more client devices;
      determine whether the at least one healthcare provider selected is an appropriate match to assign to the patient, wherein the determination is based on the skill set of the at least one healthcare provider, a healthcare provider overcapacity condition, and healthcare compliance restrictions;
      based upon the determination that the at least one healthcare provider is an appropriate match to assign to the patient:
         1. determine the period of time that the at least one healthcare provider is assigned to the patient based on the healthcare provider population profile;
         2. store in the database the assignment of the at least one healthcare provider to the patient and determine a portion of a time period of patient clinical care that is covered, wherein the portion of the time period of the patient clinical care that is covered is based on the determined period of time that the at least one healthcare provider is assigned to the patient;
         3. automatically display a first graphical representation of the assignment of the at least one healthcare provider to the patient through an assignment bar at the graphical user interface at the one or more client devices, wherein the assignment bar represents the time period of the patient clinical care, wherein the portion of the time period of the patient clinical care that is covered is indicated by a shaded portion or highlighted portion of the assignment bar and a portion of the time period of the patient clinical care that is not covered is indicated by an unshaded portion, an unhighlighted portion, or a uncolored portion of the assignment bar, wherein the portion of the time period of the patient clinical care that is covered is displayed at the graphical user interface at the one or more client devices on the assignment bar at a position representing the determined period of time that the at least one healthcare provider is assigned to the patient, and wherein the assignment bar is activatable to display an expanded assignment view at the graphical user interface which presents details of a particular at least one healthcare provider assignment corresponding to a particular portion of the assignment bar when selected;
      based upon another determination that the at least one healthcare provider is not an appropriate match to assign to the patient, generate an alert, from the at least one computing device and automatically display the alert at the graphical user interface at the one or more client devices, the alert indicating that the at least one healthcare provider is not an appropriate match to assign to the patient and includes one or more selectable action icons, wherein one or more actions related to one of one or more options are automatically initiated upon receiving selection of one of the one or more selectable action icons and the one or more options includes a first option to proceed with the assignment of the at least one healthcare provider to the patient and a second option to present alternative healthcare providers to assign to the patient; and
      upon receiving selection of one of the one or more selectable action icons relating to the second option to present alternative healthcare providers to assign to the patient, display a second graphical representation at the graphical user interface at the one or more client devices of the alternative healthcare providers to assign to the patient and to replace the at least one healthcare provider that is not an appropriate match to assign to the patient.

2. The system of claim 1, further comprising based upon the determination that the at least one healthcare provider is an appropriate match forth patient, the at least one computing device updates the assignment bar at the graphical user interface at the one or more client devices to reflect the assignment of the at least one healthcare provider to the patient.

3. The system of claim 2, wherein the at least one computing device updates the assignment bar and eliminates a coverage gap for the patient, wherein the coverage gap is a graphical representation within the assignment bar that shows the patient is not covered by the at least one healthcare provider.

4. The system of claim 1, further comprising the at least one computing device blocks out an inappropriate healthcare provider such that the inappropriate healthcare provider may not be assigned to the patient.

5. A system for managing clinical workforce operations comprising:

at least one computing device, having a processor coupled to a memory, communicating with a database and one or more client devices operated respectively by one or more operators, wherein the at least one computing device accesses the database and communicates with the one or more client devices, wherein the one or more client devices operate in a network with the at least one computing device, and each of the one or more client devices has a processor coupled to a memory;

the at least one computing device provides instructions to the one or more client devices, wherein the one or more client devices generate a graphical user interface;

wherein the at least one computing device receives one or more indications of the one or more operators' interactions respectively with the graphical user interface at the one or more client devices and do the following:

access at least one clinical care need of a patient, wherein the at least one clinical care need includes a skill set required to service a need of the patient;

access a healthcare provider population profile from the database through the at least one computing device, wherein the healthcare provider population profile includes availability of at least one healthcare provider, a skill set of the at least one healthcare provider, and a healthcare provider capacity rating of the at least one healthcare provider;

receive a selection of the at least one healthcare provider such that the at least one healthcare provider is assigned to the patient and the assignment is displayed at the graphical user interface based on a period of time that the at least one healthcare provider is assigned to the patient; wherein the selection of the at least one healthcare provider includes dragging and dropping a healthcare provider identifier object associated with the at least one healthcare provider on a patient identifier object associated with the patient at the graphical user interface at the one or more client devices;

determine whether the at least one healthcare provider selected is an appropriate match to assign to the patient, wherein the determination is based on the skill set of the at least one healthcare provider, a healthcare provider over capacity condition, and healthcare compliance restrictions;

based upon the determination that the at least one healthcare provider is an appropriate match to assign to the patient:
1. determine the period of time that the at least one healthcare provider is assigned to the patient based on the healthcare provider population profile;
2. store in the database the assignment of the at least one healthcare provider to the patient and determine a portion of a time period of patient clinical care that is covered, wherein the portion of the time period of the patient clinical care that is covered is based on the determined period of time that the at least one healthcare provider is assigned to the patient;
3. automatically display a first graphical representation of the assignment of the at least one healthcare provider to the patient with an assignment bar at the graphical user interface at the one or more client devices, wherein the assignment bar represents the time period of the patient clinical care, wherein the portion of the time period of the patient clinical care that is covered is indicated by a shaded portion or highlighted portion of the assignment bar and a portion of the time period of the patient clinical care that is not covered is indicated by an unshaded portion, an unhighlighted portion, or a uncolored portion of the assignment bar, wherein the portion of the time period of the patient clinical care that is covered is displayed at the graphical user interface at the one or more client devices on the assignment bar at a position representing the determined period of time that the at least one healthcare provider is assigned to the patient, and wherein the assignment bar is activatable to display an expanded assignment view at the graphical user interface which presents details of a particular at least one healthcare provider assignment corresponding to a particular portion of the assignment bar when selected;

based upon another determination that the at least one healthcare provider is not an appropriate match to assign to the patient, generate an alert and automatically display the alert at the graphical user interface at the one or more client devices, the alert indicating that the at least one healthcare provider is not an appropriate match to assign to the patient and includes one or more selectable action icons, wherein one or more actions related to one of one or more options are automatically initiated upon receiving selection of one of the one or more selectable action icons and the one or more options includes a first option to proceed with the assignment of the at least one healthcare provider to the patient and a second option to present alternative healthcare providers to assign to the patient; and upon receiving selection of one of the one or more selectable action icons relating to the second option to present alternative healthcare providers to assign to the patient, display a second graphical representation at the graphical user interface at the one or more client devices of the alternative healthcare providers to assign to the patient and to replace the at least one healthcare provider that is not an appropriate match to assign to the patient.

6. The system of claim 5, further comprising based upon the determination that the at least one healthcare provider is an appropriate match forth patient, the at least one computing device updates the assignment bar at the graphical user interface at the one or more client devices to reflect the assignment of the at least one healthcare provider to the patient.

7. The system of claim 6, wherein the at least one computing device updates the assignment bar and eliminates a coverage gap for the patient, wherein the coverage gap is a graphical representation within the assignment bar that shows the patient is not covered by the at least one healthcare provider.

8. The system of claim 5, further comprising the at least one computing device blocks out an inappropriate healthcare provider such that the inappropriate healthcare provider may not be assigned to the patient.

* * * * *

UNITED STATES PATENT AND TRADEMARK OFFICE
CERTIFICATE OF CORRECTION

| | |
|---|---|
| PATENT NO. | : 11,404,161 B2 |
| APPLICATION NO. | : 15/394209 |
| DATED | : August 2, 2022 |
| INVENTOR(S) | : Douglas W. Wager |

It is certified that error appears in the above-identified patent and that said Letters Patent is hereby corrected as shown below:

In the Claims

Claim 1, Column 7, Line 49:
The line reading "healthcare provider overcapacity condition, and" should read --healthcare provider over capacity condition, and--.

Claim 1, Column 8, Line 14:
The line reading "or more client devices on the assignment barat a" should read --or more client devices on the assignment bar at a--.

Claim 2, Column 8, Line 51:
The line reading "an appropriate match forth patient, the at least one comput-" should read --an appropriate match for the patient, the at least one comput- --.

Claim 6, Column 10, Line 48:
The line reading "an appropriate match forth patient, the at least one comput-" should read --an appropriate match for the patient, the at least one comput- --.

Signed and Sealed this
Fifteenth Day of November, 2022

Katherine Kelly Vidal
*Director of the United States Patent and Trademark Office*